United States Patent [19]

Meier et al.

[11] Patent Number: Plant 6,537

[45] Date of Patent: Jan. 17, 1989

[54] KENTUCKY BLUEGRASS 'BA 72-492'

[75] Inventors: Virgil D. Meier; Eugene W. Mayer, both of Marysville, Ohio

[73] Assignee: The O. M. Scott & Sons Company, Marysville, Ohio

[21] Appl. No.: 27,285

[22] Filed: Mar. 17, 1987

[51] Int. Cl.[4] ..... A01H 5/00

[52] U.S. Cl. ..... Plt./88

[58] Field of Search ..... Plt./88

*Primary Examiner*—James R. Feyrer

[57] ABSTRACT

A variety of Kentucky bluegrass having a high level of disease resistance, excellent turf performance in the sun and shade and a medium level of seed yield potential.

1 Drawing Sheet

Kentucky bluegrasses have been disclosed in U.S. Plant Pat. No. 3,156 which issued on May 9, 1972; U.S. Plant Pat. No. 3,186 which issued on May 23, 1972; U.S. Plant Pat. No. 4,336 which issued on Nov. 28, 1978; U.S. Plant patent application, Ser. No. 872,537, filed June 10, 1986; U.S. Plant patent application, Ser. No. 910,146, filed Sept. 19, 1986; and U.S. Plant patent application, Ser. No. 028,424, filed of even date herewith.

SUMMARY OF THE VARIETY

The present invention relates to a new and distinct variety of *Poa pratensis* which has been designated Ba 72-492 Kentucky bluegrass.

Ba 72-492 plant material originated by crossing a Kentucky bluegrass plant ("Gnome") disclosed in U.S. Plant patent application Ser. No. 872,537, the seed parent, with a pollen parent plant. As a result of this breeding, a distinct variety was produced and asexually propagated by rhizomes, tillers and disseminules. Seed of Ba 72-492 was produced first at Marysville, Ohio and later at Gervais, Oreg.

Asexual reproduction of Ba 72-492 by propagules (tillers and rhizomes) and by disseminules (modified caryopses produced by apomixis) has consistently produced plants indistinguishable from the mother plant.

Ba 72-492 has a number of highly desirable characteristics including a good level of resistance to Helminthosporium spp that causes leaf spot, melting out and crown rot, *Ustilago striiformis* that causes stripe smut, *Erysiphe graminis* that causes powdery mildew, and Puccinia spp. that causes rust; an attractive leafy turf type growth habit; moderately wide leaf blades; an attractive green color which can be maintained throughout the entire growing season; good turf performance as evidenced by consistently high scores in tests throughout the U.S.A. and Canada; and a medium seed yield potential in the bluegrass seed production region of the U.S.A.

In comparison with its seed parent, Gnome, the new variety is more shade tolerant and has better resistance to powdery mildew and rust. In comparison to another Kentucky bluegrass (Ba 72-500) which is disclosed in U.S. Plant patent application Ser. No. 910,146 which also has Gnome as its seed parent, Ba 72-492 produces seeds that are shorter than Ba 72-500 and the panicle of Ba 72-492 does not nod as much as Ba 72-500.

DETAILED DESCRIPTION OF THE VARIETY

Figure 1:
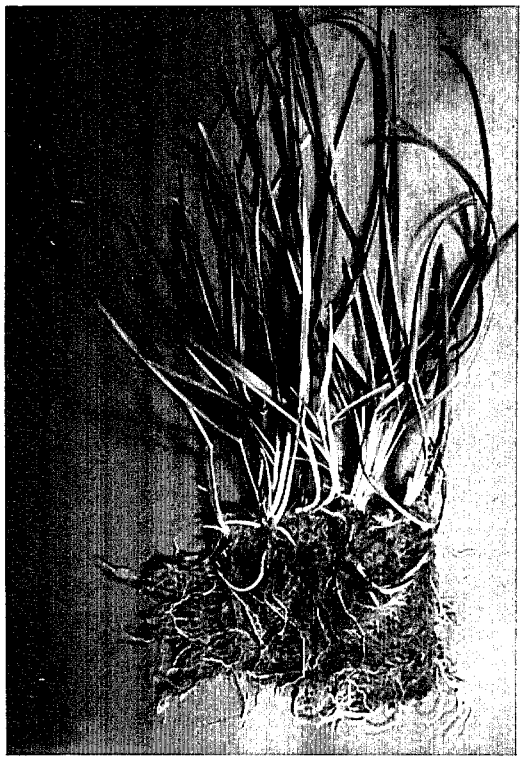
FIG. 1 is a photograph of Ba 72-492 Kentucky bluegrass plant in the vegetative stage including the extensive root and rhizome system.
Figure 2:
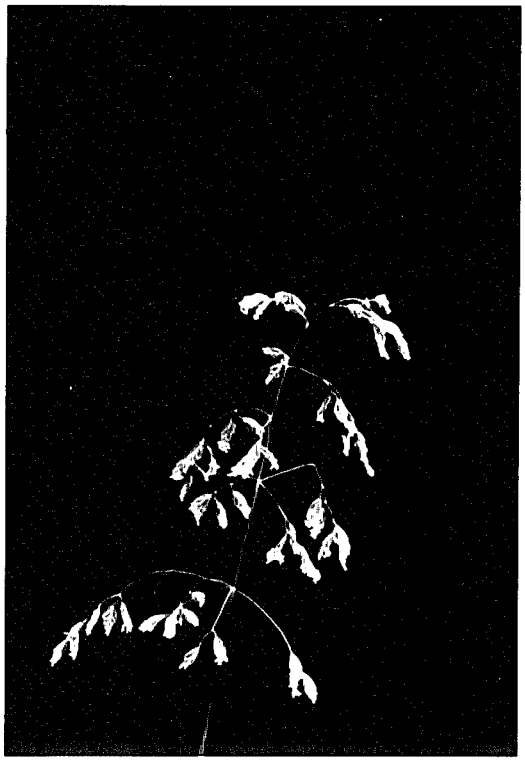
FIG. 2 is a photograph of Ba 72-492 Kentucky bluegrass panicle.
Figure 3:
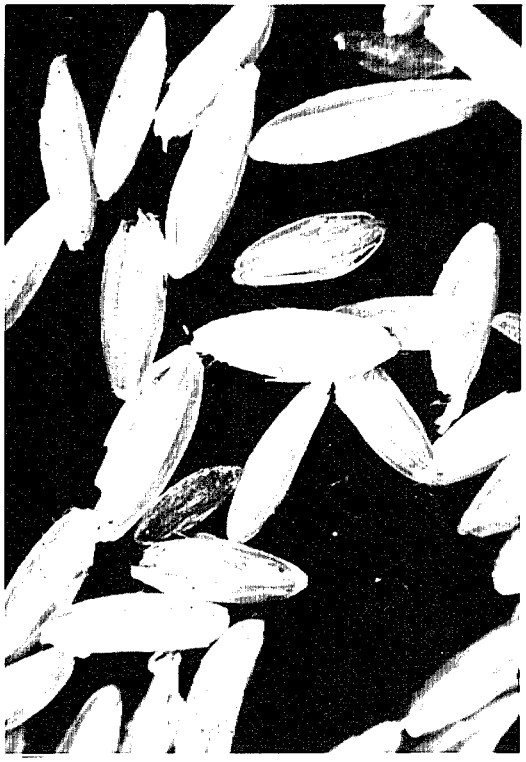
FIG. 3 is a photograph of Ba 72-492 Kentucky bluegrass seed.

Ba 72-492 Kentucky bluegrass (*Poa protensis* L.) is perennial with creeping rhizomes forming a moderately dense turf. When plants overwinter in the field with freezing temperatures and then are brought into the greenhouse during late winter to continue growth undisturbed by clipping under moderate temperatures (60°-80° F.), culms are erect averaging 486 mm in length with an average of 2.2 nodes per culm. The uppermost internode averages 10.5 cm, and the peduncle averages 12.6 cm in length and 0.552 mm in thickness. The flag leaf averages 5.2 cm in length, 3.6 mm in width and 0.117 mm in thickness. The panicle is generally erect as opposed to nodding with an average length of 12.6 cm, width of 4.2 cm, and 5.5 whorls. The lowest whorl has an average of 4.0 branches and the third whorl from the bottom of the panicle has an average of 3.0 branches. The average spikelet at the tip of a branch in the lowest whorl is 5.2 mm in length and has 4.4 florets with an outer glume of 2.9 mm and an inner glume of 3.3 mm in length. A similar spikelet from the third whorl from the bottom of the panicle is 5.0 mm in length and has 4.2 florets with an outer glume of 3.0 mm and an inner glume of 3.3 mm in length. After the seed has been conditioned, the lemma has a generally smooth keel and almost no long fine hairs at the base. The seed of Ba 72-492 is 2.53 mm in length and 0.76 mm in width with approximately 1,275,740 seeds per pound. Comparisons of Ba 72-492 with other bluegrass varieties on seed dimensions are shown in Table 1 and on seed numbers per pound are shown in Table 2.

TABLE 1

Seed Measurements of Ba 72-492 and Other Bluegrass Varieties After Conditioning

| Variety | Length (mm) | Width (mm) |
|---|---|---|
| Ba 72-492 | 2.53 | 0.76 |
| Ba 70-139 | 2.86 | 0.78 |
| Ba 72-500 | 2.77 | 0.80 |
| Baron | 3.07 | 0.86 |

TABLE 1-continued

Seed Measurements of Ba 72-492 and Other Bluegrass Varieties After Conditioning

| Variety | Length (mm) | Width (mm) |
|---|---|---|
| Bristol | 2.73 | 0.80 |
| Nassau | 2.96 | 0.78 |
| Newport | 2.76 | 0.71 |
| Park | 3.04 | 0.72 |
| Ram I | 3.51 | 0.84 |
| Victa | 3.20 | 0.86 |
| LSD (.05) | 0.19 | 0.06 |

TABLE 2

Seed Counts per Pound of Ba 72-492 and Other Bluegrass Varieties After Conditioning

| | Number of Seeds Per Pound |
|---|---|
| Ba 72-492 | 1,275,740 |
| Adelphi | 1,383,976 |
| America | 1,659,824 |
| Gnome | 1,017,641 |
| Baron | 1,051,693 |
| Birka | 1,223,530 |
| Bonnieblue | 1,135,303 |
| Bristol | 1,270,821 |
| Classic | 1,250,316 |
| Eclipse | 1,335,668 |
| Georgetown | 1,232,913 |
| Glade | 1,108,441 |
| Kenblue | 1,463,923 |
| Merit | 1,109,728 |
| Nassau | 1,127,130 |
| Newport | 1,226,481 |
| Park | 1,248,349 |
| Sydsport | 1,355,644 |
| Vantage | 1,555,303 |
| Victa | 1,038,298 |

Since environmental conditions such as soil and climate may influence morphological characters to some extent, comparisons of morphological characteristics of Ba 72-492 are made with other Kentucky bluegrass varieties in Tables 3–7.

TABLE 3

Morphological Comparisons of Ba 72-492 and Other Bluegrass Varieties Grown As Unmowed Spaced Plants in the Field at Marysville, Ohio.

| | Mature Plant Height 2 Year Mean | Leaf Blade Width Annual | Panicle Density 2 Year Mean |
|---|---|---|---|
| Ba 74-492 | 40 | 2.4 | 52 |
| A-34 | 63 | 2.4 | 61 |
| Bristol | 31 | 2.0 | 38 |
| Glade | 35 | 2.3 | 58 |
| Kenblue | 51 | 2.0 | 43 |
| Merion | 28 | 2.3 | 26 |
| Nugget | 23 | 2.1 | 34 |
| Parade | 53 | 3.0 | 67 |
| Park | 51 | 2.1 | 54 |
| P-104 | 39 | 2.4 | 33 |
| Vantage | 54 | 2.3 | 52 |
| Victa | 38 | 2.5 | 49 |

Ratings:
Mature Plant Height (cm) - includes panicles.
Leaf Blade Width - 1–4, 4 = wide blade.
Panicle Density - 1–100, 100 = high panicle density

TABLE 4

Morphological Comparison of Panicles of Ba 72-492 and Other Bluegrass Varieties in the Greenhouse at Marysville, Ohio.

| Variety | Panicle Nodding* | Panicle Length (cm) | Panicle Width (cm) | Number of Whorls Per Panicle |
|---|---|---|---|---|
| Ba 72-492 | 1.2 | 7.5 | 4.2 | 5.5 |
| Ba 70-139 | 2.0 | 6.7 | 3.7 | 4.8 |
| Ba 72-500 | 2.0 | 6.8 | 3.8 | 5.0 |
| Baron | 1.0 | 7.8 | 4.1 | 5.2 |
| Bristol | 2.0 | 9.7 | 5.0 | 5.0 |
| Nassau | 2.0 | 10.0 | 6.0 | 5.0 |
| Newport | 2.0 | 10.3 | 4.4 | 4.5 |
| Park | 1.6 | 9.0 | 3.7 | 4.0 |
| Ram I | 2.0 | 9.0 | 4.7 | 4.0 |
| Victa | 1.2 | 7.5 | 4.1 | 5.4 |
| LSD (.05) | 0.5 | 1.6 | 1.0 | 0.8 |

TABLE 4-continued

Morphological Comparison of Panicles of Ba 72-492 and Other Bluegrass Varieties in the Greenhouse at Marysville, Ohio.

| Variety | Number of Branches: Lower Whorl | Number of Branches: Third Whorl | Peduncle Length (cm) | Peduncle Width (mm) |
|---|---|---|---|---|
| Ba 72-492 | 4.0 | 3.0 | 12.6 | 0.558 |
| Ba 70-139 | 3.8 | 2.7 | 13.2 | 0.610 |
| Ba 72-500 | 4.0 | 2.4 | 12.9 | 0.660 |
| Baron | 3.8 | 2.5 | 12.7 | 0.559 |
| Bristol | 3.3 | 2.7 | 15.0 | 0.686 |
| Nassau | 3.0 | 2.0 | 8.0 | 0.533 |
| Newport | 2.3 | 2.3 | 18.0 | 0.558 |
| Park | 4.3 | 3.7 | 14.3 | 0.787 |
| Ram I | 2.5 | 2.0 | 18.5 | 0.610 |
| Victa | 4.4 | 3.4 | 12.2 | 0.711 |
| LSD (.05) | 0.7 | 0.8 | 3.7 | 0.018 |

*Panicle nodding rated 1 = erect, 2 = nodding.

TABLE 5

Morphological Comparison of Culms and Flag Leaves of Ba 72-492 and Other Bluegrass Varieties in the Greenhouse at Marysville, Ohio.

| Variety | Flag Leaf Length (cm) | Flag Leaf Width (mm) | Flag Leaf Thickness (mm) |
|---|---|---|---|
| Ba 72-492 | 5.2 | 3.6 | 0.117 |
| Ba 70-139 | 4.7 | 3.2 | 0.112 |
| Ba 72-500 | 4.1 | 3.2 | 0.112 |
| Baron | 4.5 | 3.2 | 0.119 |
| Bristol | 5.5 | 3.4 | 0.127 |
| Nassau | 6.2 | 3.1 | 0.127 |
| Newport | 6.1 | 3.5 | 0.135 |
| Park | 4.2 | 2.6 | 0.109 |
| Ram I | 4.7 | 3.1 | 0.127 |
| Victa | 5.9 | 4.0 | 0.124 |
| LSD (.05) | 1.8 | 0.6 | 0.013 |

| Variety | Top Internode Length (cm) | Culm Length (mm) | Number of Nodes Per Culm |
|---|---|---|---|
| Ba 72-492 | 10.5 | 486 | 2.2 |
| Ba 70-139 | 10.2 | 435 | 2.7 |
| Ba 72-500 | 9.8 | 439 | 2.7 |
| Baron | 10.1 | 482 | 2.5 |
| Bristol | 11.3 | 522 | 2.7 |
| Nassau | 11.2 | 450 | 2.5 |
| Newport | 11.2 | 547 | 2.3 |
| Park | 13.0 | 578 | 3.0 |
| Ram I | 10.2 | 527 | 3.0 |
| Victa | 10.6 | 474 | 2.4 |
| LSD (.05) | 2.1 | 79 | 0.6 |

TABLE 6

Morphological Comparison of Spikelets and Florets of Ba 72-492 and Other Bluegrass Varieties in the Greenhouse at Marysville, Ohio.

| Variety | Spikelet Length (mm): Lowest Whorl | Spikelet Length (mm): Third Whorl | Number of Florets per Spikelet: Lowest Whorl | Number of Florets per Spikelet: Third Whorl |
|---|---|---|---|---|
| Ba 72-492 | 5.2 | 5.0 | 4.4 | 4.2 |
| Ba 70-139 | 5.2 | 5.2 | 4.2 | 4.0 |
| Ba 72-500 | 5.1 | 5.0 | 4.2 | 3.9 |
| Baron | 5.0 | 5.0 | 3.7 | 3.8 |

TABLE 6-continued

Morphological Comparison of Spikelets and Florets of Ba 72-492 and Other Bluegrass Varieties in the Greenhouse at Marysville, Ohio.

| | | | | |
|---|---|---|---|---|
| Bristol | 6.2 | 6.0 | 5.7 | 5.3 |
| Nassau | 4.6 | 4.6 | 4.5 | 4.5 |
| Newport | 5.3 | 5.2 | 5.2 | 5.2 |
| Park | 6.5 | 6.7 | 5.2 | 4.7 |
| Ram I | 4.7 | 5.2 | 5.2 | 5.5 |
| Victa | 5.2 | 5.0 | 3.8 | 3.8 |
| LSD (.05) | 0.9 | 0.8 | 1.1 | 1.0 |

| | Glume Length (mm) | | | |
|---|---|---|---|---|
| | Outer | | Inner | |
| Variety | Lowest Whorl | Third Whorl | Lowest Whorl | Third Whorl |
| Ba 72-492 | 2.9 | 3.0 | 3.3 | 3.3 |
| Ba 70-139 | 3.2 | 3.1 | 3.5 | 3.5 |
| Ba 72-500 | 3.1 | 3.1 | 3.4 | 3.4 |
| Baron | 2.9 | 2.8 | 3.4 | 3.3 |
| Bristol | 3.4 | 3.3 | 3.7 | 3.9 |
| Nassau | 2.3 | 2.4 | 2.7 | 2.7 |
| Newport | 2.6 | 2.5 | 2.9 | 2.9 |
| Park | 3.0 | 3.2 | 3.5 | 3.7 |
| Ram I | 2.6 | 2.4 | 2.9 | 2.7 |
| Victa | 2.8 | 3.0 | 3.3 | 3.3 |
| LSD (.05) | 0.5 | 0.4 | 0.4 | 0.4 |

TABLE 7

Morphological Comparison of Leaves of Ba 72-492 and Other Bluegrass Varieties in the Greenhouse at Marysville, Ohio.

| Variety | Ligule Length (mm) | Leaf Length (mm) | Leaf Width (mm) | Leaf Angle (Degrees From Horizontal) |
|---|---|---|---|---|
| Ba 72-492 | 0.28 | 239 | 4.4 | 52 |
| Ba 70-139 | 0.26 | 218 | 4.1 | 55 |
| Ba 72-500 | 0.25 | 204 | 4.1 | 50 |
| Baron | 0.30 | 313 | 4.4 | 63 |
| Bristol | 0.30 | 253 | 4.3 | 37 |
| Nassau | 0.22 | 226 | 3.5 | 39 |
| Newport | 0.22 | 251 | 4.1 | 50 |
| Park | 0.33 | 329 | 4.2 | 44 |
| Ram I | 0.18 | 188 | 3.7 | 40 |
| Victa | 0.28 | 235 | 4.3 | 52 |
| LSD (.05) | 0.11 | 49 | 0.6 | 10 |

| Variety | Hairs[a] Around Ligule on Upper Surface of the Leaf | Hairs[a] on Collar | Hairs[b] on Ligule |
|---|---|---|---|
| Ba 72-492 | 1.0 | 3.2 | 1.3 |
| Ba 70-139 | 1.0 | 3.5 | 1.5 |
| Ba 72-500 | 1.0 | 3.5 | 2.7 |
| Baron | 1.0 | 5.0 | 4.0 |
| Bristol | 1.3 | 4.7 | 4.3 |
| Nassau | 2.7 | 5.0 | 1.0 |
| Newport | 1.0 | 4.0 | 0.8 |
| Park | 1.0 | 1.7 | 0.0 |
| Ram I | 1.0 | 3.7 | 0.3 |
| Victa | 1.0 | 3.3 | 2.2 |
| LSD (.05) | 0.3 | 1.4 | 1.8 |

[a]Hairs around ligule and on collar rated 1–5: 1 = none, 5 = many.
[b]Hairs on ligule rated 0–5: 0 = none, 5 = many.

Ba 72-492 has performed well throughout the U.S.A. and Canada as exhibited by high turf quality ratings in many different locations in comparison to other varieties as shown in Table 8.

TABLE 8

Comparison of the Turf Quality of Ba 72-492 and Other Bluegrass Varieties in the U.S.A. and Canada

| Variety | St. Louis Missouri 1 Year Mean | Winnipeg Manitoba 2 Year Mean | Beltsville Maryland 1 Year Mean | Adelphia New Jersey 2 Year Mean |
|---|---|---|---|---|
| Ba 72-492 | 3.2 | 6.4 | 5.7 | 6.2 |

TABLE 8-continued

Comparison of the Turf Quality of Ba 72-492 and Other Bluegrass Varieties in the U.S.A. and Canada

| | | | | |
|---|---|---|---|---|
| A-34 | | 6.6 | 5.6 | |
| Adelphi | 2.9 | | 5.9 | 6.4 |
| Admiral | | 6.0 | | |
| America | 2.8 | | | |
| Aquila | | 7.1 | | 5.7 |
| Banff | | | 4.8 | |
| Baron | 2.7 | 6.2 | 5.3 | 6.4 |
| Birka | 2.3 | | | 5.9 |
| Bonnieblue | | | 5.0 | 6.7 |
| Bono | | | | |
| Bristol | 2.7 | | 5.0 | 6.5 |
| Cheri | | | 5.1 | 6.0 |
| Columbia | | | 4.9 | 5.9 |
| Eclipse | | | 5.9 | 7.2 |
| Enmundi | | | 5.5 | 6.3 |
| Fylking | | | 4.9 | 5.7 |
| Geary | | | | 3.6 |
| Georgetown | | | | |
| Geronimo | | | | |
| Glade | 2.8 | | 5.3 | 6.7 |
| Gnome | 2.9 | | | 6.4 |
| Kenblue | | | | 3.3 |
| Melba | | 6.9 | | |
| Merion | | | 5.3 | 6.0 |
| Merit | 2.8 | 6.5 | 6.1 | 6.2 |
| Midnight | | | 5.5 | 7.3 |
| Monopoly | | | 4.9 | 5.7 |
| Mosa | | | | |
| Mystic | | 6.6 | | |
| Nassau | | 5.9 | 4.5 | 5.9 |
| Newport | | | | |
| Nugget | | 7.1 | | |
| Parade | | | 5.0 | 5.6 |
| Park | 1.8 | | | |
| Ram I | | | 4.6 | 6.2 |
| Rugby | | | | |
| SD Common | | | | 3.2 |
| Shasta | | 7.1 | | 5.7 |
| Sydsport | 2.7 | | 5.8 | 6.0 |
| Touchdown | 2.7 | 6.8 | 5.8 | 6.1 |
| Trampas | | 6.3 | | |
| Trenton | | | | |
| Vantage | 2.6 | | 5.5 | 3.6 |
| Victa | 2.8 | | 5.5 | 6.5 |
| Wabash | | | | 4.8 |

| Variety | Lincoln Nebraska 2 Year Mean | Agassiz British Columbia 1 Year Mean | Gervais Oregon 3 Year Mean | Marysville Ohio 5 Year Mean |
|---|---|---|---|---|
| Ba 72-492 | 6.0 | 5.5 | 2.6 | 2.8 |
| A-34 | 6.2 | | | |
| Adelphi | 6.1 | | 2.4 | 2.7 |
| Admiral | | | | |
| America | | | 2.5 | |
| Aquila | | | | |
| Banff | | | | |
| Baron | 5.6 | | | |
| Birka | 5.9 | | | |
| Bonnieblue | 5.8 | | | |
| Bono | | 5.2 | | |
| Bristol | 5.9 | 6.1 | 2.8 | 2.7 |
| Cheri | 6.3 | | | |
| Columbia | | | | |
| Eclipse | 5.8 | | | |
| Enmundi | 5.9 | | | |
| Fylking | 6.1 | | | |
| Geary | | | | |
| Georgetown | | 4.9 | | |
| Geronimo | | 5.1 | | |
| Glade | 6.4 | | 2.5 | |
| Gnome | | | 2.3 | |
| Kenblue | | | 1.4 | |
| Melba | | 5.9 | | |
| Merion | 5.9 | 5.3 | | |
| Merit | 6.0 | 4.9 | 2.4 | |
| Midnight | 5.9 | | | |
| Monopoly | | | | |
| Mosa | | | | |
| Mystic | | | | |

TABLE 8-continued

Comparison of the Turf Quality of Ba 72-492 and Other Bluegrass Varieties in the U.S.A. and Canada

| | | | | |
|---|---|---|---|---|
| Nassau | | | | |
| Newport | | | | 1.4 |
| Nugget | | | | |
| Parade | 6.5 | | | 2.7 |
| Park | 5.7 | | | 2.1 |
| Ram I | 5.9 | | | |
| Rugby | | | | |
| SD Common | | | | |
| Shasta | | | | |
| Sydsport | 6.3 | | | |
| Touchdown | 5.9 | | | |
| Trampas | | 5.7 | | |
| Trenton | 5.8 | | | 2.6 |
| Vantage | 5.7 | | 2.2 | 2.6 |
| Victa | | | | |
| Wabash | | | | |

| Variety | Prince Frederick Maryland 4 Year Mean | Somis California 1 Year Mean | Marysville Ohio 2 Year Mean |
|---|---|---|---|
| Ba 72-492 | 2.2 | 2.8 | 2.3 |
| A-34 | | | |
| Adelphi | 2.4 | | 1.9 |
| Admiral | | | |
| America | | | |
| Aquila | | | |
| Banff | | | |
| Baron | 2.4 | | |
| Birka | 1.8 | | |
| Bonnieblue | 2.3 | | |
| Bono | 1.9 | | |
| Bristol | 2.3 | 3.0 | 2.1 |
| Cheri | | | |
| Columbia | 2.5 | | |
| Eclipse | | | |
| Enmundi | | | |
| Fylking | | | |
| Geary | | | |
| Georgetown | | | |
| Geronimo | | | |
| Glade | | | 2.0 |
| Gnome | | | 2.0 |
| Kenblue | 1.8 | | |
| Melba | | | |
| Merion | | | |
| Merit | 2.3 | | |
| Midnight | 2.4 | | |
| Monopoly | | | |
| Mosa | | 2.3 | |
| Mystic | | | |
| Nassau | | | |
| Newport | | | |
| Nugget | | | |
| Parade | | | |
| Park | 2.0 | | |
| Ram I | 2.4 | | |
| Rugby | 2.2 | | |
| SD Common | | | |
| Shasta | | | |
| Sydsport | | | 2.0 |
| Touchdown | | | |
| Trampas | | | |
| Trenton | 2.4 | | |
| Vantage | 2.3 | | |
| Victa | 2.3 | 2.5 | 2.0 |
| Wabash | | | |

Rating Scale: Larger number indicates higher quality.

In addition, Ba 72-492 tolerates shady growing conditions very well which is an important characteristic that allows an even broader range of use. Comparisons of Ba 72-492 and other varieties for shade performance are found in Table 9 and Table 10.

TABLE 9

Turf Performance Ratings Under Natural Shade of Ba 72-492 and Other Bluegrass Varieties at Marysville, Ohio

| | Quality | | | | 4 Yr |
|---|---|---|---|---|---|
| | Year 1 | Year 2 | Year 3 | Year 4 | Mean |
| Ba 72-492 | 2.2 | 2.6 | 2.5 | 2.6 | 2.5 |
| Merion | 1.8 | 1.6 | 2.0 | 1.8 | 1.8 |
| Fylking | 1.8 | 1.9 | 1.9 | 2.0 | 1.9 |
| A-34 | 2.0 | 2.2 | 2.6 | 2.7 | 2.4 |
| Park | 1.7 | 1.8 | 1.9 | 2.0 | 1.9 |
| Newport | 1.9 | 1.7 | 1.9 | 2.1 | 1.9 |
| Bristol | 1.8 | 2.1 | 2.2 | 1.8 | 2.0 |
| Enmundi | 2.0 | 2.0 | 2.2 | 2.5 | 2.2 |
| Bonnieblue | 2.0 | 1.7 | 2.0 | 1.7 | 1.9 |
| Touchdown | 1.8 | 2.1 | 2.1 | 1.7 | 1.9 |
| Aquila | 1.8 | 1.7 | 1.7 | 2.1 | 1.8 |
| Parade | 1.8 | 2.0 | 2.2 | 1.8 | 2.0 |
| Victa | 2.0 | 1.5 | 1.8 | 2.0 | 1.8 |
| LSD (.05) | | .46 | | .47 | |

Rated 1–4, 4 = Best

TABLE 10

Turf Performance Ratings Under Natural Shade of Ba 72-492 and Other Bluegrass Varieties at Gervais, Oregon

| | Year 1 | | | | Quality Year 2 | | |
|---|---|---|---|---|---|---|---|
| | June | Aug. | Oct. | Mean | Feb. | Sept. | Mean |
| Ba 72-492 | 3.3 | 3.2 | 2.8 | 3.1 | 2.5 | 2.8 | 2.7 |
| Bristol | 2.5 | 2.8 | 2.3 | 2.6 | 3.0 | 1.7 | 2.4 |
| Gnome | 3.5 | 1.0 | 1.0 | 1.8 | 1.0 | 0.5 | .8 |
| Victa | 2.8 | 1.8 | 1.7 | 2.1 | 2.0 | 1.8 | 1.9 |
| LSD(.05) | .97 | .97 | .63 | | .95 | .96 | |

| | Year 3 Feb. | Year 4 May | 4 Yr Mean |
|---|---|---|---|
| Ba 72-492 | 2.2 | 1.8 | 2.5 |
| Bristol | 2.0 | 2.3 | 2.3 |
| Gnome | 1.3 | 2.3 | 1.6 |
| Victa | 1.8 | 1.0 | 1.7 |
| LSD(.05) | .83 | .80 | |

Rated 1–4, 4 = Best

The new variety has a pleasant medium green color which can be maintained throughout the growing season and widely scattered locations in the U.S.A. and Canada as shown by the comparative test results in Table 11.

TABLE 11

Comparison of Turf Color of Ba 72-492 and Other Bluegrass Varieties at Various Locations in the U.S.A. and Canada.

| Variety | St. Louis Missouri 1 Year Mean | Truro Nova Scotia 1 Year Mean | Winnipeg Manitoba 1 Year Mean | Lincoln Nebraska 2 Year Mean | Agassiz British Columbia 1 Year Mean |
|---|---|---|---|---|---|
| Ba 72-492 | 9.2 | 7.1 | 7.2 | 7.0 | 5.7 |
| A-34 | | | 6.3 | 6.5 | |
| Adelphi | 9.4 | | | 7.2 | |
| America | 9.4 | | | 7.0 | |
| Aquila | | | 7.3 | 6.7 | |
| Baron | 9.2 | | 7.3 | 6.9 | |
| Birka | 9.1 | | | 6.7 | |
| Bonnieblue | | | | 7.0 | |
| Bono | 9.0 | | | | 6.0 |
| Bristol | 9.5 | | | 7.3 | 7.0 |
| Cheri | | | | 7.0 | |
| Eclipse | | | | 7.0 | |
| Enmundi | | | | 7.0 | |
| Fylking | | | | 6.8 | |
| Georgetown | | | | | 6.2 |
| Geronimo | | | | | 5.8 |
| Glade | 9.3 | | | 7.1 | |
| Gnome | 9.3 | 7.5 | | | |
| Kenblue | | | | | |
| Melba | | 6.9 | | | |
| Merion | | | | 6.9 | 5.7 |

TABLE 11-continued

Comparison of Turf Color of Ba 72-492 and Other Bluegrass Varieties at Various Locations in the U.S.A. and Canada.

| | | | | | |
|---|---|---|---|---|---|
| Merit | 9.2 | | 7.2 | 7.0 | 6.5 |
| Midnight | | | 8.1 | 7.9 | |
| Mystic | | | 6.5 | | |
| Nassau | | | 7.2 | | |
| Newport | | | | | |
| Nugget | | | 7.3 | | |
| Parade | | | | 6.8 | |
| Park | 9.0 | | | 6.1 | |
| Ram I | | | | 7.3 | |
| Rugby | | | | 6.8 | |
| Shasta | | | 7.2 | | |
| Sydsport | 9.2 | | | 7.0 | |
| Touchdown | 9.0 | | 6.6 | 6.8 | |
| Trampas | | 6.9 | | | |
| Vantage | 9.2 | | | 6.8 | |
| Victa | 9.2 | 7.5 | | 6.9 | |

| Variety | Gervais Oregon 3 Year Mean | Marysville Ohio 4 Year Mean | Prince Frederick Maryland 4 Year Mean | Somis California 1 Year Mean |
|---|---|---|---|---|
| Ba 72-492 | 6.9 | 7.2 | 7.6 | 6.7 |
| A-34 | | | | |
| Adelphi | 7.6 | | 7.4 | |
| America | 7.6 | | | 6.5 |
| Aquila | | | | |
| Baron | | | | |
| Birka | | | | 6.3 |
| Bonnieblue | | | | |
| Bono | | | | 6.2 |
| Bristol | 9.3 | 7.8 | 8.3 | 7.6 |
| Cheri | | | | |
| Eclipse | | | | |
| Enmundi | | | | |
| Fylking | | 6.6 | | |
| Georgetown | | | | |
| Geronimo | | | | |
| Glade | 8.3 | | 8.0 | 7.0 |
| Gnome | 7.4 | | | |
| Kenblue | 6.6 | 7.2 | | 5.8 |
| Melba | | | | |
| Merion | | 6.9 | | |
| Merit | 7.4 | 7.1 | 7.4 | 5.8 |
| Midnight | | | | 5.5 |
| Mystic | | | | |
| Nassau | | | | |
| Newport | 7.5 | 7.0 | | 6.0 |
| Nugget | | | | |
| Parade | | | | |
| Park | | | 6.8 | |
| Ram I | | | | 7.3 |
| Rugby | | | | 6.7 |
| Shasta | | | | |
| Sydsport | | 7.1 | | |
| Touchdown | | | | |
| Trampas | | | | |
| Vantage | | 6.9 | 6.8 | 5.7 |
| Victa | 7.1 | 7.1 | 7.6 | 6.0 |

Rating Scale: Larger number indicates darker green color.

Turf diseases are one of the major causes of inconsistent and poor turf performance among locations and years. Comparisons of resistance to leaf spot (also known as melting out and crown rot) caused by *Helminthosporium vagans,* powdery mildew caused by *Erysiphe graminis,* rust caused by Puccinia spp., dollarspot caused by *Sclerotina homeocarpa,* and red thread caused by *Corticium fuciform* are presented in Tables 12,13,14,15,16 and 17, respectively.

TABLE 12

Comparison of Leafspot Disease Incidence on Ba 72-492 and Other Bluegrasses at Several Locations in the U.S.A. and Canada.

| | St. Louis[a] | Beltsville[b] | Adelphia[b] | Agassiz[c] British |
|---|---|---|---|---|

TABLE 12-continued

Comparison of Leafspot Disease Incidence on Ba 72-492 and Other Bluegrasses at Several Locations in the U.S.A. and Canada.

| Variety | Missouri 1 Year Mean | Maryland 1 Year Mean | New Jersey 1 Year Mean | Columbia 1 Year Mean |
|---|---|---|---|---|
| Ba 72-492 | 3 | 8.3 | 6.3 | 3.0 |
| A-34 | | 5.3 | 4.3 | |
| Adelphi | 2 | 8.0 | 5.7 | |
| America | 8 | | | |
| Aquila | | | 6.3 | |
| Banff | | 5.3 | 7.0 | |
| Baron | 2 | 7.0 | 8.7 | |
| Birka | 5 | | 6.3 | |
| Bonnieblue | | | 7.0 | |
| Bono | 7 | | | 3.0 |
| Bristol | 2 | 7.0 | 8.3 | 2.3 |
| Cheri | | 6.3 | | |
| Columbia | | 5.7 | 6.3 | |
| Eclipse | | 7.7 | 9.0 | |
| Enmundi | | 7.0 | | |
| Fylking | | 6.7 | 6.3 | |
| Geary | | | 2.0 | |
| Georgetown | | | | 4.3 |
| Geronimo | | | | 4.7 |
| Glade | 2 | 7.3 | 6.3 | |
| Gnome | 2 | 7.0 | 8.0 | |
| Kenblue | | 3.3 | 1.7 | |
| Merion | | 6.3 | 7.7 | 3.0 |
| Merit | 3 | 7.3 | 7.7 | |
| Midnight | | 7.0 | 7.0 | |
| Monopoly | | 5.3 | 6.0 | |
| Nassau | | 7.7 | 7.4 | |
| Newport | | | | |
| Parade | | 6.0 | 5.0 | |
| Park | 52 | | | |
| Ram I | | 6.5 | 7.0 | |
| Regent | | | | 3.7 |
| Rugby | | | 5.0 | |
| Shasta | | | 6.0 | |
| Sydsport | 3 | 7.3 | 6.3 | |
| Touchdown | 7 | 7.7 | | |
| Trenton | | | 6.0 | |
| Vantage | 7 | 5.0 | 2.0 | |
| Victa | 2 | 8.0 | 7.0 | |
| Wabash | | | 2.0 | |
| LSD (.05) | 7 | | 1.9 | |

| Variety | Gervais[a] Oregon 3 Year Mean | Marysville[1] Ohio 5 Year Mean | Marysville[a] Ohio(Shade) 1 Year Mean |
|---|---|---|---|
| Ba 72-492 | 22 | 4 | 0 |
| A-34 | | | |
| Adelphi | 46 | 9 | |
| America | 29 | | 0 |
| Aquila | | | |
| Banff | | | |
| Baron | | | |
| Birka | | | 0 |
| Bonnieblue | | | |
| Bono | | | |
| Bristol | 8 | 5 | 2 |
| Cheri | | | |
| Columbia | | | |
| Eclipse | | | |
| Enmundi | | | |
| Fylking | | | |
| Geary | | | |
| Georgetown | | | |
| Geronimo | | | |
| Glade | 46 | | 0 |
| Gnome | 76 | | 0 |
| Kenblue | 75 | | 67 |
| Merion | | | |
| Merit | 65 | | |
| Midnight | | | |
| Monopoly | | | |
| Nassau | | | |
| Newport | 45 | | |
| Parade | | 10 | |
| Park | | 54 | |
| Ram I | | | |

TABLE 12-continued

Comparison of Leafspot Disease Incidence on Ba 72-492 and Other Bluegrasses at Several Locations in the U.S.A. and Canada.

| | | | |
|---|---|---|---|
| Regent | | | |
| Rugby | | | |
| Shasta | | | |
| Sydsport | | | |
| Touchdown | | | 0 |
| Trenton | | | |
| Vantage | | 15 | |
| Victa | 70 | 7 | 0 |
| Wabash | | | |
| LSD (.05) | 15 | 5 | 4 |

Ratings
[a]% of turf affected by disease
[b]1-9, 9 = least disease
[c]1-9, 9 = most disease

TABLE 13

Comparison of Powdery Mildew Disease Incidence on Ba 72-492 and Other Bluegrasses.

| | Gervais | Natural Shade[b] | |
|---|---|---|---|
| Variety | Oregon 1 Year Mean | Marysville Ohio 3 Year Mean | Marysville Ohio 2 Year Mean |
| Ba 72-492 | 5 | 3 | 5 |
| A-34 | | | |
| Adelphi | | | |
| America | | | 7 |
| Banff | | 15 | |
| Birka | | | 2 |
| Bristol | 3 | 10 | 1 |
| Eclipse | | | 3 |
| Geronimo | | | 40 |
| Glade | | 37 | 21 |
| Gnome | 78 | | 61 |
| Kenblue | | | 2 |
| Merion | | | |
| Monopoly | | 2 | |
| Mosa | | | |
| Newport | | 33 | |
| Nugget | | | |
| Parade | | | |
| Park | | | |
| Rugby | | 15 | |
| Touchdown | | | 0 |
| Vantage | | | |
| Victa | 35 | 47 | 52 |
| LSD (.05) | 21 | 16 | 6 |

| Variety | Prince Frederick Maryland 1 Year Mean | Spaced Plants - Sun[b] Marysville Ohio 2 Year Mean |
|---|---|---|
| Ba 72-492 | 2 | 14 |
| A-34 | 2 | 52 |
| Adelphi | 12 | 23 |
| America | | |
| Banff | | |
| Birka | | |
| Bristol | 1 | 15 |
| Eclipse | | |
| Geronimo | | |
| Glade | 57 | 8 |
| Gnome | | |
| Kenblue | | 20 |
| Merion | | 12 |
| Monopoly | | |
| Mosa | 58 | |
| Newport | | |
| Nugget | | 5 |
| Parade | | 5 |
| Park | | 15 |
| Rugby | | |
| Touchdown | | |
| Vantage | | 34 |
| Victa | 25 | 14 |
| LSD (.05) | 13 | |

[a]Rated 0-9,9 = least disease
[b]Rated as % of turf affected by disease

TABLE 14

Comparison of Stem Rust (*Puccinia graminis*) Disease Incidence on Ba 72-492 and Other Bluegrasses at Adelphia, New Jersey

| | |
|---|---|
| Ba 72-492 | 7.9 |
| Midnight | 7.0 |
| Columbia | 6.7 |
| Banff | 6.5 |
| Bristol | 7.7 |
| Parade | 6.2 |
| Monopoly | 7.1 |
| Ram I | 7.0 |
| Victa | 5.6 |
| Merit | 5.7 |
| Baron | 6.4 |
| Nassau | 6.8 |
| Eclipse | 4.7 |
| Aquila | 6.9 |
| Bonnieblue | 5.4 |
| Adelphi | 7.1 |
| America | 7.4 |
| Vantage | 6.2 |
| Touchdown | 3.5 |
| Birka | 3.5 |
| Merion | 2.4 |
| LSD (.05) | 0.9 |

Rated 1-9, 9 = No disease

TABLE 15

Comparison of Rust (Puccinia spp.) Disease Incidence on Ba 72-492 and Other Bluegrasses.

| Variety | Turf Aggasiz[a] British Columbia 2 Year Mean | Gervais[b] Oregon 1 Year Mean | Unmowed Spaced Plants Marysville[b] Ohio 2 Year Mean |
|---|---|---|---|
| Ba 72-492 | 1.2 | 2 | 9 |
| A-34 | | | 12 |
| Adelphi | | 23 | 10 |
| America | | 9 | |
| Bono | 2.1 | | |
| Bristol | 1.2 | 6 | 17 |
| Geronimo | 1.5 | | |
| Glade | | 4 | 11 |
| Gnome | | 13 | |
| Kenblue | | 30 | 23 |
| Merion | 2.8 | | 16 |
| Merit | 2.9 | 8 | |
| Newport | | 23 | |
| Nugget | | | 12 |
| Parade | | | 15 |
| Park | | | 25 |
| Vantage | | | 36 |
| Victa | | 9 | 14 |
| LSD (.05) | | 12 | |

[a]Rated 1-9, 9 = most disease
[b]Rated as % of disease incidence

TABLE 16

Comparison of Dollarspot Incidence on Ba 72-492 and Other Bluegrasses.

| Variety | Prince Frederick Maryland | Marysville Ohio |
|---|---|---|
| Ba 72-492 | 9 | 60 |
| Adelphi | 8 | 20 |
| America | | 13 |
| Baron | 50 | 23 |
| Birka | 6 | 47 |
| Bonnieblue | 10 | |
| Bono | 4 | 63 |
| Bristol | 6 | 17 |
| Columbia | 10 | |
| Eclipse | | 8 |
| Glade | | 40 |
| Gnome | | 22 |
| Kenblue | 8 | 37 |
| Merit | 4 | |
| Midnight | 6 | |

TABLE 16-continued

Comparison of Dollarspot Incidence on Ba 72-492 and Other Bluegrasses.

| Variety | Prince Frederick Maryland | Marysville Ohio |
|---|---|---|
| Park | | 33 |
| Ram I | 40 | |
| Rugby | 12 | |
| Sydsport | | 43 |
| Touchdown | | 50 |
| Trenton | 28 | |
| Vantage | 11 | 15 |
| Victa | 5 | 23 |
| Wabash | 11 | |
| LSD (.05) | 19 | 24 |

Rating: % of turf that is affected by disease.

TABLE 17

Comparison of Red Thread Disease Incidence on Ba 72-492 and Other Bluegrasses at Gervais, Oregon.

| | Red Thread |
|---|---|
| Ba 72-492 | 7 |
| Victa | 10 |
| Bristol | 0 |
| Glade | 15 |
| Adelphi | 0 |
| Kenblue | 23 |
| Newport | 3 |
| America | 2 |
| Merit | 7 |
| Gnome | 0 |
| LSD (.05) | 13 |

Rating: % of turf affected by disease

Tests in Maryland and Ohio indicate that Ba 72-492 is not highly susceptible to stripe smut caused by *Ustilago striiformis* since some unreleased selections of bluegrass had a high incidence of stripe smut but Ba 72-492 was not affected.

The new variety has a low growth habit and a slower vertical growth rate than many varieties and especially the common type of varieties such as Park, Kenblue and Newport, as indicated by comparisons in Table 18, which should allow it to tolerate lower mowing heights and possibly decrease the total number of mowings per year without sacrificing overall turf performance.

TABLE 18

Comparison of Growth Habit of Ba 72-492 and Other Bluegrasses at Marysville, Ohio.

| Variety | Test 1 1 Year Mean[a] | Test 2 2 Year Mean[a] | Test 3 3 Year Mean[b] |
|---|---|---|---|
| Ba 72-492 | 2.0 | 1.4 | 74 |
| Adelphi | 2.0 | 2.4 | |
| America | 1.8 | | |
| Baron | 1.8 | | |
| Birka | 2.0 | | |
| Bono | 2.0 | | |
| Bristol | 2.0 | 2.0 | 74 |
| Eclipse | 2.0 | | |
| Fylking | | | 93 |
| Glade | 2.2 | | |
| Gnome | 2.0 | | |
| Kenblue | 2.9 | | 96 |
| Merion | | | 78 |
| Merit | | | 84 |
| Newport | | | 100 |
| Parade | | 2.2 | |
| Park | 2.9 | 2.2 | |
| Sydsport | 1.9 | | 72 |
| Touchdown | 2.0 | | |
| Vantage | 2.7 | 2.0 | 84 |
| Victa | 1.9 | 2.0 | 77 |

TABLE 18-continued

Comparison of Growth Habit of Ba 72-492 and Other Bluegrasses at Marysville, Ohio.

| Variety | Test 1 1 Year Mean[a] | Test 2 2 Year Mean[a] | Test 3 3 Year Mean[b] |
|---|---|---|---|
| LSD (.05) | 0.3 | 0.5 | 12 |

[a]Rated 1–5, 5 = high growth, 1 = dwarf.
[b]Rated as height (mm) of turf about one week after last mowing.

The leaf texture of Ba 72-492 is similar to many bluegrass varieties when maintained under mowed turf conditions as the comparisons show in Table 19.

TABLE 19

Comparison of Leaf Texture of Ba 72-492 and Other Bluegrasses Under Mowed Turf Conditions.

| Variety | St. Louis Missouri | Agassiz British Columbia | Marysville Ohio |
|---|---|---|---|
| Ba 72-492 | 4.0 | 6.0 | 5.0 |
| Adelphi | 5.3 | | |
| America | 6.0 | | |
| Baron | 4.6 | | |
| Birka | 6.0 | | |
| Bono | 5.6 | 6.7 | |
| Bristol | 5.3 | 7.0 | 5.0 |
| Fylking | | | 5.8 |
| Geronimo | | 5.7 | |
| Glade | 6.0 | | |
| Gnome | 4.3 | | |
| Kenblue | | | 5.5 |
| Merion | | 6.3 | 5.0 |
| Merit | 4.3 | 5.0 | 5.0 |
| Newport | | | 5.0 |
| Park | 6.0 | | |
| Sydsport | 5.0 | | 5.0 |
| Touchdown | 5.0 | | |
| Vantage | 6.0 | | 5.3 |
| Victa | 4.4 | | 4.8 |
| LSD (.05) | 0.7 | | 0.4 |

Rating: 1–9, 9 = finest texture.

Ba 72-492 has a medium level of seed yielding ability which should make it an economically feasible variety to produce for commercial markets as shown in Table 20.

TABLE 20

Seed Yield Comparisons of Ba 72-492 and Other Bluegrass Varieties in Oregon

| | Gervais | | | La Grande | | | |
|---|---|---|---|---|---|---|---|
| Variety | Year 1 | Year 2 | Mean | Year 1 | Year 2 | Mean | Madras Year 1 |
| Ba 72-492 | 585 | 864 | 725 | 1025 | 846 | 936 | 875 |
| Ba 72-500 | 559 | 757 | 658 | 876 | 857 | 867 | 1113 |
| Victa | 780 | 1394 | 1087 | 1419 | 1200 | 1310 | 1324 |
| Newport | 435 | 1256 | 846 | | | | |
| Bristol | 347 | 808 | 578 | 1089 | 970 | 1030 | |
| Mosa | 322 | 1060 | 691 | | | | |
| Julia | 296 | 1016 | 656 | | | | 1194 |
| Trampas | | | | | | | 388 |
| LSD (.05) | 140 | 134 | | 149 | 181 | 220 | |

Ratings: Pounds per acre of conditioned seed.

The low susceptibility of Ba 72-492 to rust and lodging under typical seed field conditions should aid in producing economical seed crops as noted by the comparative results on Table 21.

TABLE 21

Plant Characteristics of Ba 72-492 and Other Bluegrass Varieties at Gervais, Oregon Under Seed Production Conditions.

| | Rust | Lodging | |
|---|---|---|---|
| | Year 1 | Year 1 | Year 2 |
| Ba 72-492 | 1 | 2.5 | 0.2 |

TABLE 21-continued

Plant Characteristics of Ba 72-492 and Other Bluegrass Varieties at Gervais, Oregon Under Seed Production Conditions.

| | Rust | Lodging | |
|---|---|---|---|
| | Year 1 | Year 1 | Year 2 |
| Victa | 2 | 2.0 | 0 |
| Bristol | 4 | 4.0 | 1 |
| Newport | 4 | 4.0 | 1 |
| Mosa | 4 | 2.0 | 0 |

TABLE 21-continued

Plant Characteristics of Ba 72-492 and Other Bluegrass Varieties at Gervais, Oregon Under Seed Production Conditions.

| | Rust | Lodging | |
|---|---|---|---|
| | Year 1 | Year 1 | Year 2 |
| Julia | 4 | 5.0 | 4 |

Ratings
Rust: 1–4, 4 = very susceptible
Lodging: 0–5, 5 = severe lodging

What is claimed is:

1. A variety of Kentucky bluegrass plant, substantially as shown and described, characterized particularly by a high level of resistance to diseases, a desirable green color throughout the growing season, a high quality persistent turf under a wide range of environmental conditions including shady conditions and a medium level of seed yielding capacity.

* * * * *